United States Patent
Wang et al.

(10) Patent No.: US 10,669,156 B1
(45) Date of Patent: Jun. 2, 2020

(54) SYNTHESIS OF HIERARCHICAL ZEOLITES BY SOLID STATE CRYSTALLIZATION OF ALUMINOSILICATE NANOGELS

(71) Applicant: Louisiana Tech Research Corporation, Ruston, LA (US)

(72) Inventors: Shengnian Wang, Ruston, LA (US); Yuxin Wang, Ruston, LA (US)

(73) Assignee: Louisiana Tech Research Corporation, Ruston, LA (US)

( * ) Notice: Subject to any disclaimer, the term of this patent is extended or adjusted under 35 U.S.C. 154(b) by 0 days.

(21) Appl. No.: 16/447,417

(22) Filed: Jun. 20, 2019

Related U.S. Application Data

(63) Continuation-in-part of application No. 15/683,257, filed on Aug. 22, 2017, now Pat. No. 10,343,926.

(60) Provisional application No. 62/486,511, filed on Apr. 18, 2017, provisional application No. 62/377,864, filed on Aug. 22, 2016.

(51) Int. Cl.
| | |
|---|---|
| C01B 39/04 | (2006.01) |
| C01B 39/40 | (2006.01) |
| B01J 29/06 | (2006.01) |
| B01J 29/40 | (2006.01) |
| B01J 29/44 | (2006.01) |
| C07C 1/20 | (2006.01) |
| B01J 35/00 | (2006.01) |
| B01J 37/02 | (2006.01) |
| B01J 37/03 | (2006.01) |

(52) U.S. Cl.
CPC ............... *C01B 39/40* (2013.01); *B01J 29/06* (2013.01); *B01J 29/40* (2013.01); *B01J 29/44* (2013.01); *C01B 39/04* (2013.01); *B01J 35/0013* (2013.01); *B01J 37/0201* (2013.01); *B01J 37/033* (2013.01); *C01P 2004/61* (2013.01); *C01P 2004/62* (2013.01); *C07C 1/20* (2013.01)

(58) Field of Classification Search
CPC ..... C01B 39/04; C01B 39/40; C01P 2004/61; C01P 2004/62; B01J 29/06; B01J 29/40; B01J 29/44; B01J 35/0013; B01J 37/0201; B01J 37/033
See application file for complete search history.

(56) References Cited

U.S. PATENT DOCUMENTS 10,343,926 B1 * 7/2019 Wang .................... B01J 29/041

OTHER PUBLICATIONS

Wan, Zhijian, et al. "Direct synthesis of hierarchical ZSM-5 zeolite and its performance in catalyzing methanol to gasoline conversion." Industrial & Engineering Chemistry Research 53.50 (2014): 19471-19478.

(Continued)

*Primary Examiner* — David M Brunsman
(74) *Attorney, Agent, or Firm* — Jones Walker LLP

(57) ABSTRACT

Hierarchically porous ZSM-5 zeolites, having macropores, mesopores, and micropores are formed using a solid-state crystallization process. An aluminosilicate nanogel prepared with precursors, solvent, and a structure-directing agent is provided. The solvent is evaporated from the aluminosilicate nanogel at room temperature. The dried aluminosilicate nanogel is then heated to promote crystallization. The crystallized zeolites are calcined to remove the structure-directing agent.

20 Claims, 11 Drawing Sheets

(56) References Cited

OTHER PUBLICATIONS

Mohammadparast, Farshid, Rouein Halladj, and Sima Askari. "The synthesis of nano-sized ZSM-5 zeolite by dry gel conversion method and investigating the effects of experimental parameters by Taguchi experimental design." Journal of Experimental Nanoscience 13.1 (2018): 160-173.

Tao, Haixiang, et al. "Highly stable hierarchical ZSM-5 zeolite with intra-and inter-crystalline porous structures." Chemical engineering journal 225 (2013): 686-694.

Kumar, Sandeep, et al. "A structural resolution cryo-TEM study of the early stages of MFI growth." Journal of the American Chemical Society 130.51 (2008): 17284-17286.

Beniash, Elia, et al. "Amorphous calcium carbonate transforms into calcite during sea urchin larval spicule growth." Proceedings of the Royal Society of London. Series B: Biological Sciences 264.1380 (1997): 461-465.

Gong, Yutao UT, et al. "Phase transitions in biogenic amorphous calcium carbonate." Proceedings of the National Academy of Sciences 109.16 (2012): 6088-6093.

\* cited by examiner

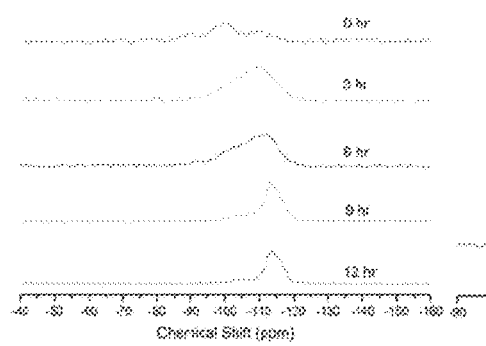
FIG. 5A
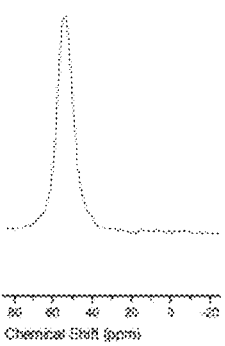
FIG. 5C
FIG. 5E
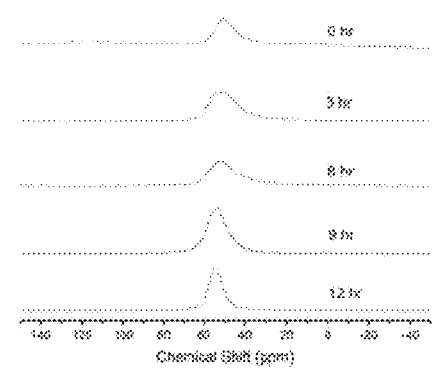
FIG. 5B
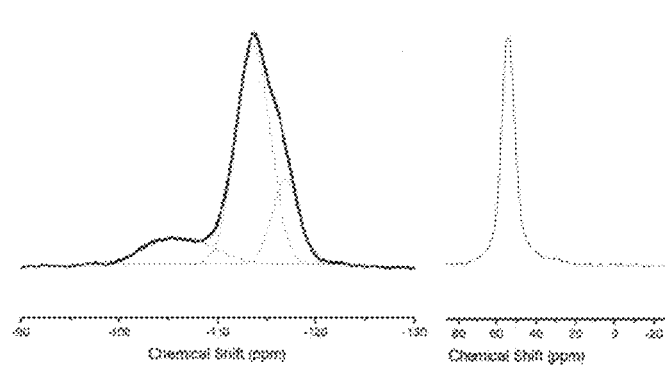
FIG. 5D
FIG. 5F
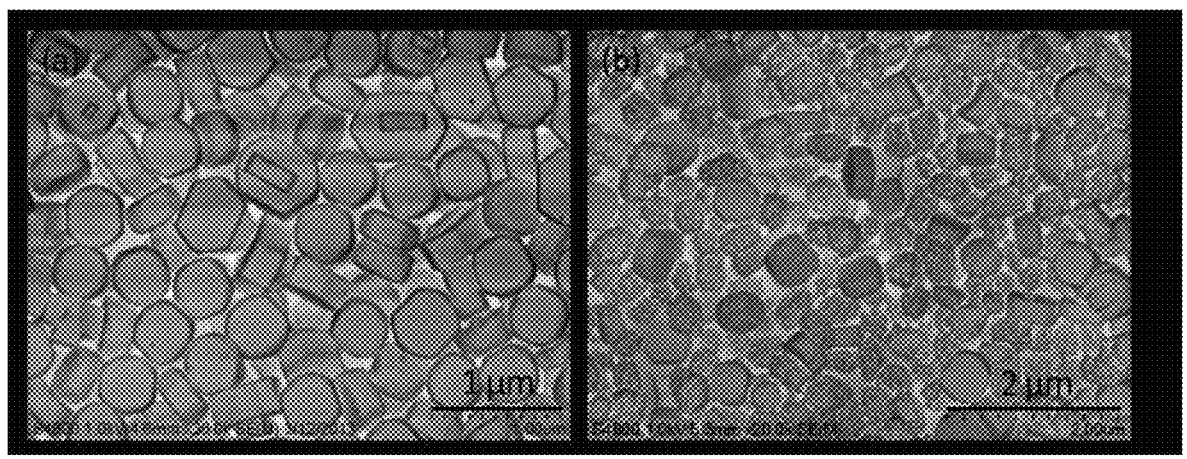
FIG. 6A        FIG. 6B FIG. 11A
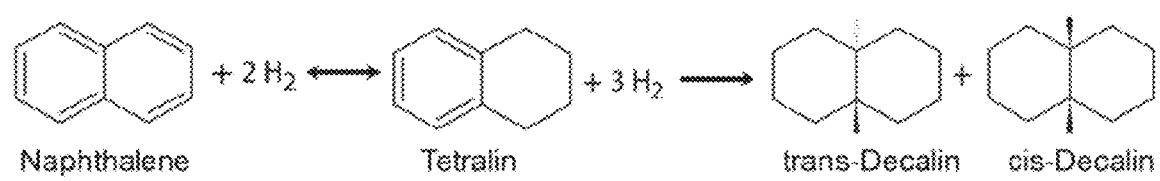
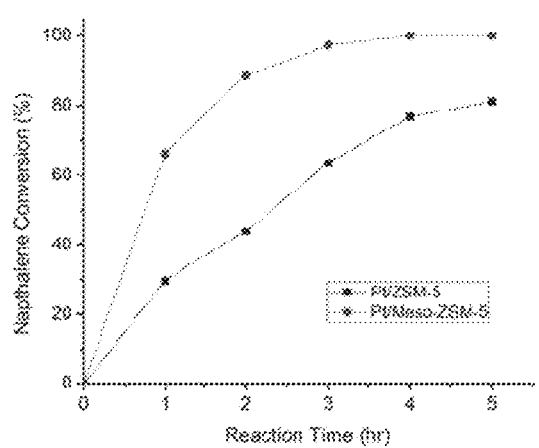
FIG. 11B
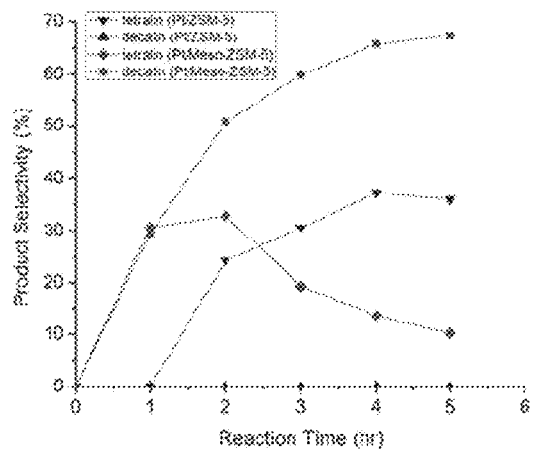
FIG. 11C FIG. 12A
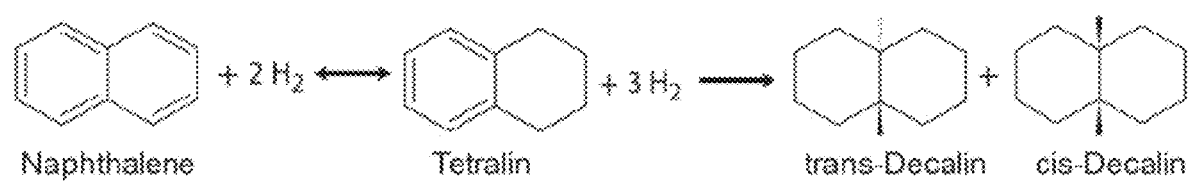
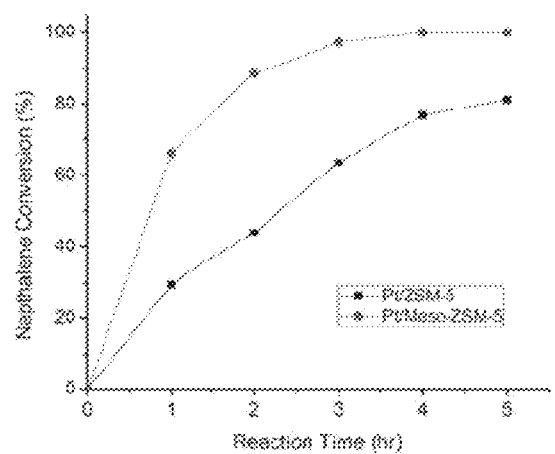
FIG. 12B
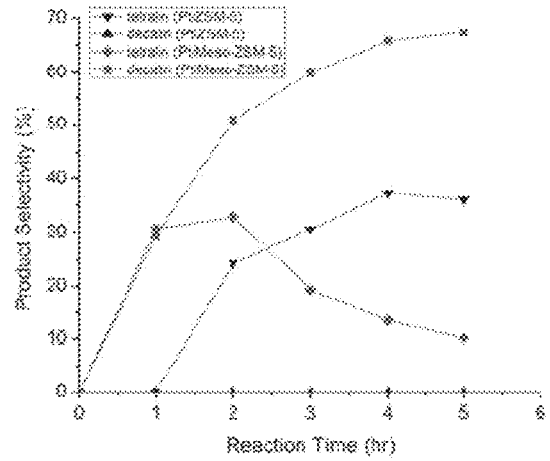
FIG. 12C

US 10,669,156 B1

SYNTHESIS OF HIERARCHICAL ZEOLITES BY SOLID STATE CRYSTALLIZATION OF ALUMINOSILICATE NANOGELS

CROSS-REFERENCE TO RELATED APPLICATIONS

This application is a continuation-in-part of U.S. Nonprovisional Patent Application No. 15/683,257, filed Aug. 22, 2017, which claims the benefit of and priority to U.S. Provisional Patent Application No. 62/377,864, filed on Aug. 22, 2016 and U.S. Provisional Patent Application No. 62/486,511, filed on Apr. 18, 2017, which are fully incorporated herein by reference.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles in accordance with the present invention. Advantages of embodiments of the present invention will be apparent from the following detailed description of the exemplary embodiments thereof, which should be considered in conjunction with the accompanying drawings in which:

FIGS. 5A to 5E depict, respectively, solid-state MAS NMR spectra of Meso-ZSM-5 with (5A, 5B) showing $^{29}Si$ and $^{27}Al$ NMR patterns of samples during solid-state crystallization, (5C, 5D) showing $^{29}Si$ and $^{27}Al$ NMR patterns of Meso-ZSM-5, and (5E, 5F) showing $^{29}Si$ and $^{27}Al$ NMR for conventional ZSM-5.

FIGS. 6A and 6B are SEM images of samples with (6A) showing aluminosilicate nanogels prepared at high pH value (about pH 14) followed by solid-state crystallization and (6B) showing aluminosilicate nanogels prepared at a lower pH value (less than about pH 12) followed by traditional hydrothermal treatment.

FIGS. 10C and 10D depict the product distribution in the lignin ethanolysis of Meso-ZSM-5 and conventional ZSM-5 with (10C) showing the overall product distribution and (10D) showing the product distribution of the aromatics.

FIG. 11A depicts ethanolysis under supercritical conditions.

FIGS. 11B and 11C depict napthalene conversion (11B) and product selectivity (11C) of Meso-ZSM-5 after lignin ethanolysis reaction under supercritical conditions.

FIG. 12A depicts a schematics of hydrogenation of naphthalene.

FIGS. 12B and 12C depict (12B) the kinetics of naphthalene conversion, and (12C) the product selectivity in naphthalene hydrogenation of Pt/Meso-ZSM-5 and Pt/conventional ZSM-5.

DETAILED DESCRIPTION OF THE INVENTION

Figure 1:
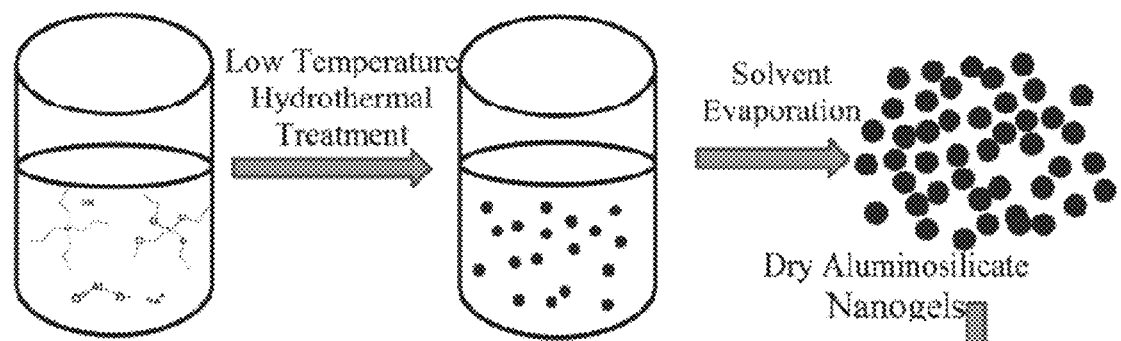
FIG. 1 is a schematic of the method for synthesizing a hierarchically porous ZSM-5 zeolite using solid-state crystallization.
Figure 1:
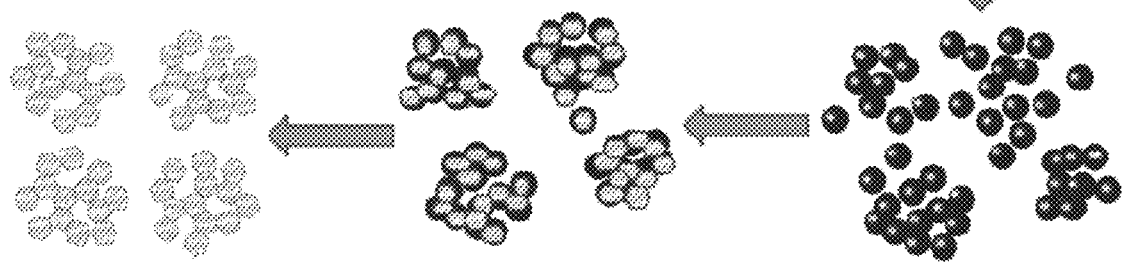

Detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually and appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. As used herein, the terms "a" or "an" are defined as one or more than one. The term "plurality," as used herein, is defined as two or more than two. The term "another," as used herein, is defined as at least a second or more. The terms "comprises," "comprising," and any other variation thereof are intended to cover a non-exclusive inclusion, such that a process, method, article, or apparatus that comprises a list of elements does not include only those elements, but may include other elements not expressly listed or inherent to such process, method, article, or apparatus. An element proceeded by "comprises ... a"

does not, without more constraints, preclude the existence of additional identical elements in the process, method, article, or apparatus that comprises the element. The terms "including," "having," and "featuring," as used herein, are defined as comprising (i.e., open language). As used herein, the term "about" or "approximately" applies to all numeric values, whether or not explicitly stated. These terms generally refer to a range of numbers ±1%-5% of the stated number that one of skill in the art would consider equivalent to the recited values (i.e., having the same function or result). In many instances these terms may include numbers that are rounded to the nearest significant figure. Relational terms such as first and second, and the like, may be used solely to distinguish one entity or action from another entity or action without necessarily requiring or implying any actual such relationship or order between such entities or actions.

Herein various embodiments of the present invention are described. To avoid redundancy, repetitive description of similar features may not be made in some circumstances. It shall be understood, however, that description of a first-appearing feature applies to the later described similar feature and each respective description, therefore, is to be incorporated therein without such repetition.

Described now are exemplary embodiments of a hierarchically porous zeolite and methods of synthesizing a hierarchically porous zeolites. Zeolites are crystalline aluminosilicates. Their solid acidity and porous structure enable zeolites to function as heterogeneous catalysts with superior selectivity based on the shape and/or chemical configuration of molecules in various chemical reactions including, but not limited to, alkylation, aromatization, cracking, pyrolysis, and hydrodesulfurization. Zeolites include micropores (pores that are approximately less than 2 nm in diameter) defined by the zeolite's unique crystal structure. However, when zeolites that only include micropores are used as a catalyst in reactions involving bulky reactants/products, there is often a serious diffusion problem inside the zeolite crystalline structure, resulting in pore blocking issues including the inability of the bulky reactants/products to diffuse through the pores.

Introducing mesopores (pores that are between approximately 2-50 nm in diameter) or a staged hierarchical porosity (a structure with inter-connected micropores, mesopores, and macropores (pores that are greater than approximately 50 nm in diameter)) to the zeolite crystalline structure may increase the catalytic activity of the zeolites in reactions with bulky reactants/products.

A hierarchically porous zeolite and methods of making a hierarchically porous zeolite are disclosed herein. In one embodiment, a method is used to synthesize hierarchically porous zeolites with MFI structure, including but not limited to hierarchically porous ZSM-5 zeolites (referred to herein as Meso-ZSM-5), without the use of meso-template materials or a solvent-involved crystallization environment. MFI refers to the MFI structure type of zeolites as defined by the Structure Commission of the International Zeolite Association. ZSM-5 zeolites are described in U.S. Pat. No. 3,702,886, which is fully incorporated herein by reference, as compositions that can be identified in terms of the mole ratios of oxides as follows: $0.9 \pm 0.2 M_{2/n} : W_2O_3 : 5\text{-}100 YO_2 : zH_2O$, wherein M is a cation, n is the valence of the cation, W is selected from the group consisting of aluminum and gallium, Y is selected from the group consisting of silicon and germanium, and z is from 0 to 40. FIG. 1 is a schematic illustration of the one embodiment of the method disclosed herein. For example, the method can include: (a) providing aluminosilicate nanogels that were made using a sol-gel process involving only precursor compounds, a structure directing agent, and solvent(s) (i.e., water or ethanol); (b) evaporating the solvent from the aluminosilicate nanogels, for instance, at room temperature, to form dry nanogels that are between about 10-30% water by weight; (c) solid crystallization of the dry nanogels (e.g., crystallization induced by heat and water stored in nanogels, but without adding water or any other solvent in liquid or vapor format) at about atmospheric pressure or slightly higher than atmospheric pressure. Alternatively, the method further includes preparing the aluminosilicate nanogel using a sol-gel process at relatively low temperature and using only precursor compounds, a structure directing agent, and solvent(s). The method can also include grinding the dry aluminosilicate nanogels into a powder prior to solid crystallization. A structure directing agent is a compound that is capable of guiding the formation of particular types of pores and/or channels during zeolite synthesis.

In one example, the method results in solid phase crystallization, in which amorphous aluminosilicate nanogels are transformed into crystallized zeolites using water stored in the individual nanogels. Accompanied with hydrolysis and condensation of Si—Al tetrahedral, adjacent nanogels are brought together as large ensembles simultaneously by weak, solid-solid interactions. With the crystallization extending to the edge of nanogels, the newly formed crystals align their crystalline patterns with the surrounding nanocrystals and eventually join into a single piece, large crystalline zeolite. The self-assembly of the nanoparticles results in stacking of these nanocrystals which creates many inter-lattice mesoscale spaces and pathways inside the produced monolithic zeolites.

In one embodiment, a method of making zeolites includes preparing aluminosilicate nanogel particles by creating a solution by mixing precursors, a structure directing agent, and a solvent, hydrolysis and aging of the solution at a relatively low temperature (less than about 90° C.) until at least 95% of the formed aluminosilicate nanogel particles are 100 nm or less, evaporating the solvent from the solution for instance at room temperature to produce dried aluminosilicate nanogel particles, heating the dried aluminosilicate nanogel particles to start the solid crystallization process that transforms the dried nanogel particles into crystallized zeolites, and then optionally calcining the crystallized zeolites between about 450° and 650° C. to remove the structure directing agent and make the crystalized zeolites more stable. In one embodiment, the temperatures for the hydrolysis step is preferably between approximately 70° C. and 90° C. Alternatively, the method can include providing a pre-prepared aluminosilicate nanogels that were mixed using only precursors, a structure directing agent, and a solvent. In still another embodiment, the dried aluminosilicate nanogels are ground into a powder prior to heating.

In embodiments that include the preparation of aluminosilicate nanogels, precursor compounds are mixed with a structure-directing agent and a solvent to form the nanogel particles. When preparing the aluminosilicate nanogels, the pH value is determined by the quantity of the structural directing agent, pH adjustment agent (for instance NaOH), and water. Generally, the pH value is less than about 12. The precursor compounds are compounds capable of providing aluminum atoms (an aluminum containing precursor) and/or silicon atoms (a silicon containing precursor). Examples of aluminum containing precursors that can be used to make the aluminosilicate nanogel particles include: $NaAlO_2$ or $C_9H_{21}AlO_3$. Examples of silicon containing precursors include: tetraethylorthosilicate or $SiO_2$. The solvent can be water, or ethanol, or any other solvent that can be used in zeolite synthesis. A structure-directing agent is also added to the mixture and incorporated into the nanogel. Examples of structure-directing agents include tetrapropyl ammonium hydroxide and tetrapropyl ammonium bromide. If tetrapropyl ammonium hydroxide is used as the structure-directing agent and $NaAlO_2$ and tetraethylorthosilicate are used as precursors, then one these compounds can be mixed so that the molar ratio is 0.25 tetrapropyl ammonium hydroxide: 0.03 $Al_2O_3$:$SiO_2$:80 $H_2O$. The final ratio of silicon to aluminum can be 15, 100, or any value therebetween. Alternatively, the final ratio of silicon to aluminum is about 30 in one case with an initial molar ratio of 0.25TPAOH: 0.03$Al_2O_3$: $SiO_2$:80$H_2O$.

In one embodiment, the aluminosilicate nanogels are prepared by dissolving tetrapropyl ammonium hydroxide and $NaAlO_2$ in water to create a solution. Then, tetraethylorthosilicate is added to the solution under strong agitation. For example, the solution may preferably be agitated for 2-4 hours at a rate of between 200 rpm and 800 rpm, at about room temperatures (between about 20° C. and 25° C). The solution can be agitated at a rate of about 600 rpm. After stopping agitation, the solution is then loaded and sealed in a container and heated at a temperature of about 70° C. to 90° C. for 12-24 hours, resulting in the formation of the aluminosilicate nanogels. Alternately, the solution is sealed and heated at a temperature of about 70° C. to 90° C. until the solution is substantially clear. In still another embodiment, the solution is heated at a temperature of about 70° C. to 90° C. for about 12-24 hours. In one embodiment, the solution is heated at a temperature of about 80° C. for 14 hours. In one embodiment, the solution is heated at a temperature between about 70° C. and 90° C. until at least 90% of the formed aluminosilicate nanogels have a diameter less than about 100 nm. In still another embodiment, the solution is heated at a temperature between about 70° and 90° C. for at least 12 hours. In a further embodiment, the solution is heated at a temperature between about 70° and 90° C. for no more than 36 hours. As used herein, the term diameter means the widest dimension or region, regardless of whether the object is spherical.

The solution is then left at room temperature (approximately 20-25° C.) to allow the solvent in the solution to evaporate to form dry nanogel particles. In one embodiment, the dried nanogels have 10-30% water content by weight. For example, the solution can be left at least about 12 hours or overnight for the solvent to evaporate. Alternately, the solution can be left to dry at room temperature between about 12 and 24 hours. In one embodiment, the solution is left at room temperature until between about 99% and 99.9% of the solvent in the solution (by weight) evaporates (e.g., 0.1% to 30%, or simply less than 30% solvent by weight). After drying, the dry nanogels are transferred to a glass or plastic container which can be sealed tightly and is structurally stable at 90-180° C. and heated to begin the solid state crystallization. Alternatively, prior to heating the dried nanogels are ground into a powder, where the individual nanogel particles have a preferred average diameter of 100 nm or less. In one embodiment, between 75% and 90%, or any subrange therebetween, of the nanogel particles formed have an average diameter of about 20-30 nm.

The dried nanogels or powder are then heated at about atmospheric pressure (or alternatively slightly higher than atmospheric pressure) and at a temperature of between about 90° C. and 180° C. for at least 6 hours to begin the solid state crystallization. In one embodiment, the dried nanogels or powder are heated at about 140°. The dried nanogels or powder also can be heated longer than 6 hours to increase the percentage of crystallization. For example, the dried nanogels or powder can be heated for at least 9 hours or at least 12 hours. After the heating process, zeolite crystals are formed. The dried nanogels or powder can be heated until at least 60% zeolite crystallization is complete (at least 60% of the dried nanogel or powder has undergone solid-state crystallization to form zeolite crystals), at least 99% zeolite crystallization is complete, or any subrange therebetween. In many embodiments, the formed crystallized zeolites have particle diameters between 200 nm and 2 μm, but there could be embodiments where the zeolites have particle diameters of any size equal to or less than 15 μm.

In one embodiment of the method, the crystallized zeolites are then dried at a temperature of between about 100° C. and 120° C. for at least 2 hours. The drying time may be longer or shorter depending on the temperatures used. For example, the crystallized zeolites may be kept at about 100° C. for about 4 hours to remove the adsorbed solvent. In another embodiment, the crystallized zeolites are heated until substantially all of the adsorbed solvent is removed, e.g., heated at 150° C. or less. Alternatively, this step can be combined with the calcination step described below.

In one embodiment, the crystallized zeolites are then calcined at a temperature ranging from about 450° C. to 650° C. for at least about 4 to 6 hours to remove the structure directing agent and any other organic compounds that may be present. Additionally, calcination improves the stability of the crystallized zeolites. In one embodiment, the calcining step is performed for about 6 hours at about 500° C. Alternatively, the calcining step is performed until substantially all of the structure-directing agent is removed. In the calcination process, the heating rate may be from about 1° C./min to 10° C./min to raise the temperature until the calcination temperature is reached. For example, the heating rate may be 1° C. per minute. In one embodiment, the zeolite crystals are washed in water to a neutral pH value and dried prior to the calcination step.

If desired, ion-exchange and further calcinations can be performed to convert the zeolites from Na-type to H-type to promote its solid acidity. For instance, the zeolite crystals can be ion-exchanged at least once with 0.1 M $NH_4NO_3$ solution at a liquid/solid ratio of about 10 $cm^3/g$ under magnetic agitation of between about 400 rpm and 600 rpm between about 80° C. and 100° C. for between about 80 and 100 minutes. In one embodiment, the zeolite crystals are ion-exchanged three times with a 0.1 M $NH_4NO_3$ solution at about 90° C. for about 90 minutes with a liquid/solid ratio of approximately 10 $cm^3/g$ under magnetic agitation at about 500 rpm. After the ion-exchange, the zeolite crystals are filtered, extensively washed with distilled water, and dried preferably at between about 90° C. and 100° C. for between 2 and 12 hours. In one embodiment, the zeolite crystals were dried at about 100° C. for about 4 hours. Then the zeolites are calcined at a temperature preferably between about 400° C. and 600° C. for between about 5 and 7 hours to form H-type zeolites. In one example, the zeolites are calcined at about 500° C. for approximately 6 hours.

Experimental Results. For the following experiments, Tetrapropyl ammonium hydroxide (TPAOH, 1 M in $H_2O$), sodium aluminate ($NaAlO_2$, ~8% $H_2O$, >99%), tetraethylorthosilicate (TEOS, >99%), benzene (>99%), benzyl alcohol (>99%), lignin (alkali), ethanol ($C_2H_5OH$, >99.5%), naphthalene ($C_{10}H_8$, >99%), and n-hexadecane (n-$C_{16}H_{34}$, >99%) were purchased from Sigma-Aldrich and used as received without further purification.

Zeolite Synthesis - Meso-ZSM-5 zeolites were synthesized by mixing TPAOH, NaAlO$_2$, TEOS, and H$_2$O with a molar ratio of 0.25TPAOH:0.03Al$_2$O$_3$:SiO$_2$:80H$_2$O. TPAOH and NaAlO$_2$ were first dissolved in H$_2$O, followed by adding TEOS under strong agitation (i.e., 600 rpm) at room temperature (between about 20° C. and 25° C.). After addition of the TEOS, the mixture was removed from agitation and kept at 80° C. until a clear solution was obtained (at least about 12 hours), which was left in hood overnight at room temperature allowing for solvent evaporation. The dry gel was then collected and ground into powders and the as-prepared dry gel powders were then transferred to a Teflon-lined autoclave for crystallization at 140 ° C. for 12 hours without adding any water. While an autoclave was used, an autoclave or other high-pressure vessel is not required for the solid-state crystallization process because no significant pressure is generated, unlike the traditional hydrothermal or steam-assisted zeolite crystallization in which 1-4 MPa steam pressure is presented in autoclave, depending on the filling volume. In the method described herein, containers that are capable of tight seal at elevated temperature (e.g., air-tight glass or plastic laboratory bottles) and resistant to basic liquids can be used. Autoclaves were used here for the comparison convenience with the hydrothermal synthesis of traditionally-prepared microporous ZSM-5 (e.g., considering the consistence on internal temperature, the heating and cooling rates). Without washing, the fully crystallized zeolites were dried at 100° C. for 4 hours to remove the adsorbed water and calcined at 500° C. for 6 hours (at a heating rate of 1° C./min) for structure stabilization and the removal of TPAOH. Conventional ZSM-5 zeolites with a similar Si/Al ratio (i.e., 33) were synthesized via traditional hydrothermal method at 140° C. for 48 hours.

All zeolite samples (Meso-ZSM-5 and traditionally-prepared microporous ZSM-5) were ion-exchanged three times with a 0.1 M NH$_4$NO$_3$ solution at 90° C. for 90 minutes with a liquid/solid ratio of 10 cm$^3$/g under magnetic agitation (500 rpm). After that, samples were filtered, extensively washed with distilled water, and dried at 100° C. for 4 hours. The H-type zeolites were obtained by calcined at 500° C. for 6 hours. The hydrothermal stability of zeolites was tested at 150° C. for 72 hours in an autoclave with a water/zeolite ratio of 50.

Pt/Zeolite Catalyst Preparation—Pt/ZSM-5 and Pt/Meso-ZSM-5 catalysts were prepared by conventional incipient wetness impregnation. Briefly, an H$_2$PtCl$_6$.6H$_2$O (99%, Sigma-Aldrich) aqueous solution (10 mL, containing 26.6 mg H$_2$PtCl$_6$.6H$_2$O) was added dropwise to wet H-type zeolite powder (1.0 g) at room temperature and the suspension was further diluted with deionized water to a total volume of 50 mL under agitation (200 rpm). After 3 hours of stirring, the suspension was left still, allowing for solvent evaporation. The dried Pt/ZSM-5 and Pt/Meso-ZSM-5 catalysts were then each transferred to a furnace for further drying at 120° C. for 12 hours and calcined at 500° C. for 4 hours (with a heating rate of 1.5° C./min). Prior to use, the Pt/ZSM-5 and Pt/Meso-ZSM-5 catalysts were each reduced in a flow of H$_2$ for 3 hours at 450° C., using a heating rate of 2.5° C./min.

Characterization—X-ray diffraction (XRD) analysis was done on a Bruker D8 diffractometer, using Cu-K$\alpha$ radiation at room temperature and instrumental settings of 40 kV and 40 mA. Data were recorded in the 2θ range of 5-60° with an angular step size of 0.02°. The crystallinity of the synthesized zeolites was quantified by taking the value of the integrated area from the XRD peaks in the 2θ range of 22.5-25°. These peaks appeared early during the crystallization process with clear peak boundary for accurate calculation. The relative crystallinity of Meso-ZSM-5 was calculated by comparing their integrated peak area with that of purely microporous ZSM-5 as follows:

$$\% \text{ Crystallinity} = \frac{\text{Peak Area (sample of Meso-ZSM-5)}}{\text{Peak Area (Reference ZSM-5)}} \times 100\%.$$

Solid-state magic angle spinning nuclear magnetic resonance (MAS NMR) spectra were recorded with a single pulse experiment on a 9.4 T (400 MHz 1H) wide bore magnet using Bruker AV console and 4 mm probe. The $^{29}$Si experiments were done with single 4-μs pulse, a relaxation delay of 60 seconds, and a MAS spinning rate of 8 kHz. Each $^{29}$Si spectrum was collected with 256 scans. The $^{27}$Al experiments were done with a pulse length of 0.33 μs, a recycle delay of 0.1 seconds, and 14 kHz MAS rate. Each $^{27}$Al spectrum was collected with 4096 scans. The $^{29}$Si and $^{27}$Al spectra were reported relative to tetrakis (trimethylsilyl)silane (TTMSS) and Al(NO$_3$)$_3$, respectively. Some NMR spectra were deconvoluted using Gaussian function.

Scanning electron microscopy (SEM) images were taken on a Hitachi S-4800. Samples were prepared by dusting the obtained zeolites onto double sided carbon tape and mounted on an alumina stub. All samples were subsequently sputter coated with a thin gold film to reduce charging effects. Transmission electron microscopy (TEM) and selected-area electron diffraction (ED) measurements were carried out on a JEOL 2010F instrument, operating at 200 kV. The samples were suspended in ethanol and dispersed on a copper grid coated with lacey carbon film before TEM analysis.

Nitrogen adsorption isotherms were obtained at −196° C. on a Micromeritics ASAP 2020 Surface Area and Porosity Analyzer in a relative pressure range from 0.05 to 0.99 relative pressure. Before measurement, samples were degassed at 300° C. for 6 hours. The pore size distribution was calculated using the Nonlocal Density Functional Theory (NLDFT) method from the adsorption branch.

The ammonia temperature programmed desorption (NH$_3$-TPD) was used to measure the acidity of zeolites on a Micromeritics AutochemII Chemisorption Analyzer. Zeolite materials (50 mg) were pretreated at 300° C. for 1 hour and then cooled down to 50° C. in an argon flow of 20 cm$^3$/min. Pure NH$_3$ (at a flow rate of 20 cm$^3$/min) was injected until adsorption saturation, followed by argon purging for another 1 hour. The desorption of NH$_3$ was monitored in the range of 50-700° C. with a heating rate of 10° C./min by a thermal conductivity detector.

Thermo-gravimetric analysis (TGA) was used to quantify water carried by dry nanogel powder to the second solid-state crystallization step using a TGA 2050 Thermogravimetric Analyzer (TA Instruments, Inc.). To distinguish water left in dry nanogel from those through adsorption, some dry nanogel powders were left in a high-purity argon-filled glove box (with water content <0.1 ppm) for a week to remove the adsorbed water in nanogels. The weight loss of nanogel samples was monitored through a thermal scanning from 30 to 110° C. at a ramp rate of 10° C./min in air atmosphere.

Catalytic reaction tests—The benzylation of benzene with benzyl alcohol was carried out at 80° C., with 0.15 g H-type zeolites, 34 mL benzene, and 0.5 mL benzyl alcohol in a three-necked round-bottom flask equipped with a reflux condenser. Samples were taken every hour and analyzed by gas chromatography (VARIAN CP-3800 GC with an FID detector using a 30 meter packed HP-5 column). The conversion was calculated based on benzyl alcohol quantity.

The catalytic conversion of Kraft lignin was carried out at 280° C. for 6 hours in a high-pressure batch reactor (Col-Int Tech, 200 mL). For each run, 1.0 g lignin, 0.5 g H-type zeolites, and 100 mL ethanol were first loaded in the reactor and the sealed reactor was then evacuated and purged with high-purity nitrogen gas for three times at room temperature. The reactor temperature was then raised to 280° C. with the reactor pressure reaching ~8 MPa. After the reaction was carried out for 6 hours, the liquid was filtered and taken for product identification and analysis on a gas chromatograph-mass spectrum (GC-MS) instrument (Agilent 7890A-5975C). Benzyl alcohol (0.1 vol% in ethanol, 1.0 μL) was added in the product samples (1 mL) before GC-MS analysis, serving as the known internal standard in GC-MS spectra to normalize the peak area for each compound. The solid was collected and weighted to calculate the overall lignin conversion.

The hydrogenation of naphthalene on Pt/ZSM-5 and Pt/Meso-ZSM-5 catalysts was performed in a large high-pressure batch reactor (Col-Int Tech, 400 mL). As the hydrogenation of naphthalene and its intermediate product (i.e., tretalin) is exothermic, the generated heat can be quickly removed by the internal cooling coil of this bigger reactor to maintain the reaction temperature. It also allows taking samples while the reactor is in operation at elevated temperature and pressure conditions to obtain the reaction kinetics. For each experiment, 33 mg of naphthalene was dissolved in n-hexadecane (99%, Sigma-Aldrich) of 100 mL and the solution was loaded in the reactor, together with 0.5 g Pt/Meso-ZSM-5 or Pt/ZSM-5. After loading, the reactor was sealed tightly and the stirring speed was set to 1,000 rpm. The reactor was heated with an electric heating jacket to the desired temperature (about 200° C.) (approximately 1 hour) and the hydrogenation was studied at 200° C. with a hydrogen pressure of 7.5 MPa. Samples were taken every hour of a total of 5 hour reaction period and were filtered through a syringe filter prior to GC-MS analysis.

Results and Discussion

Figure 2A:
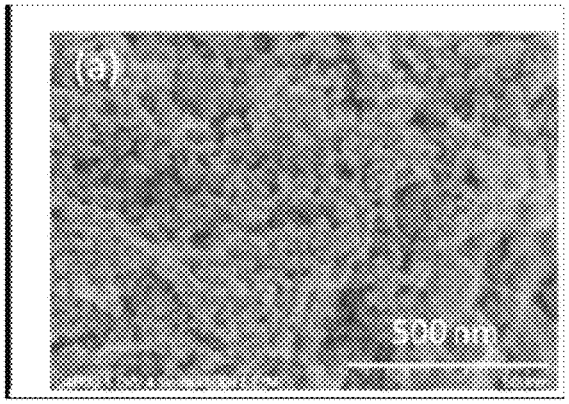
FIGS. 2A to 2F are, respectively, SEM images of the aluminosilicate particle samples that have been crystallized for (2A) 0 hours, (2B) 3 hours, (2C) 6 hours, (2D) 9 hours, and (2E, 2F) 12 hours, respectively.
Figure 2B:
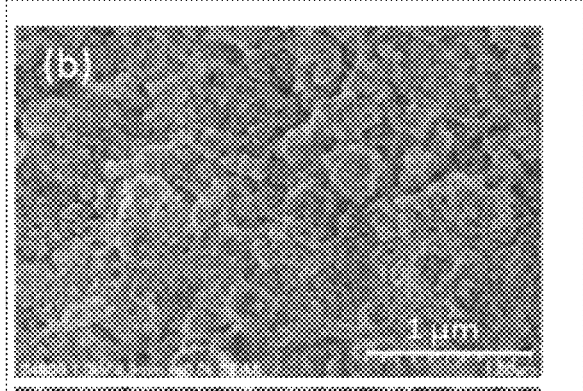
Figure 2C:
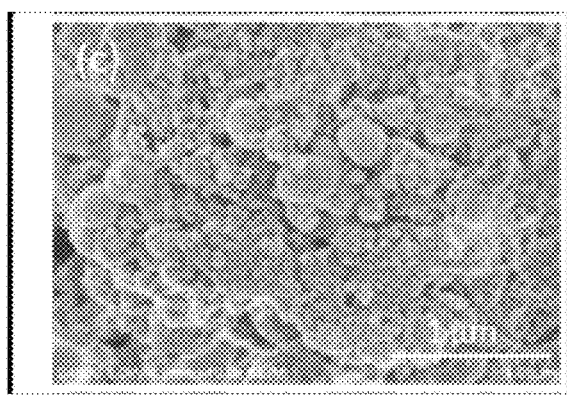
Figure 2D:
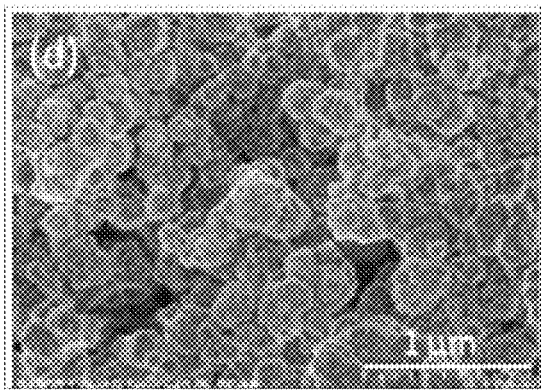
Figure 2E:
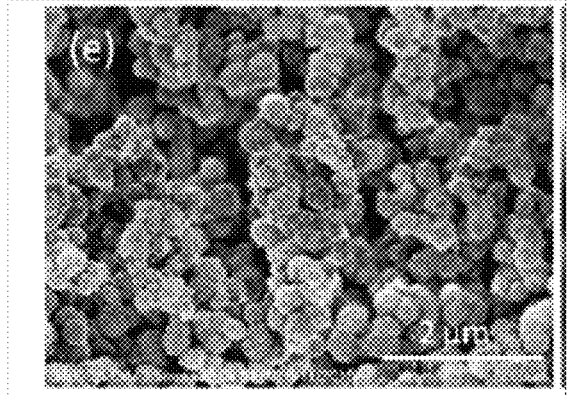
Figure 2F:
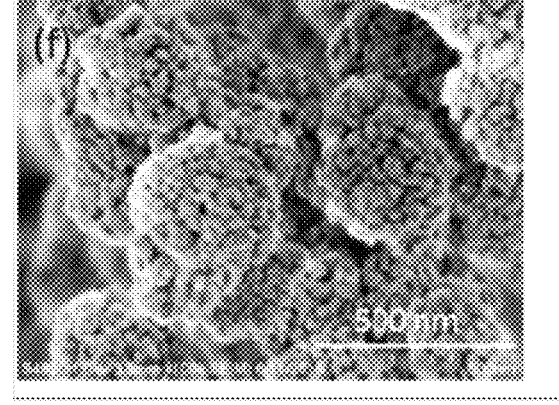
Figure 3A:
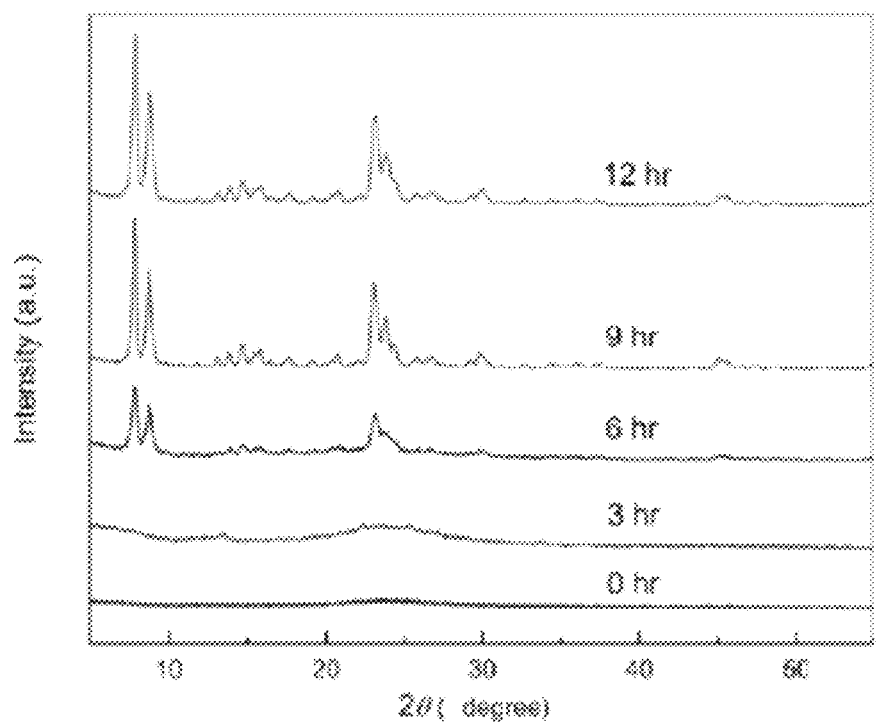
FIG. 3A depicts XRD patterns of the aluminosilicate particle samples that were crystallized for 0 hours, 3 hours, 6 hours, 9 hours, and 12 hours.
Figure 3B:
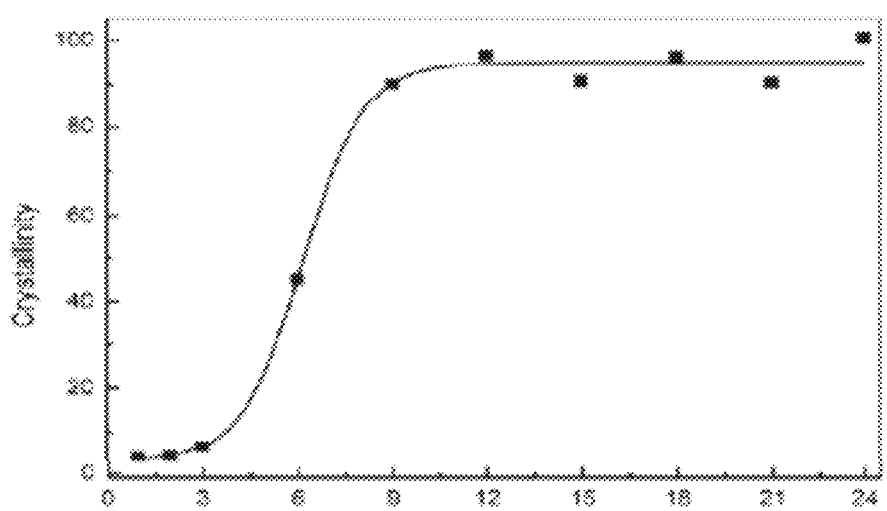
FIG. 3B depicts the relative crystallinity kinetics for the samples of FIG. 3A based on the crystallization time.
Figure 4A:
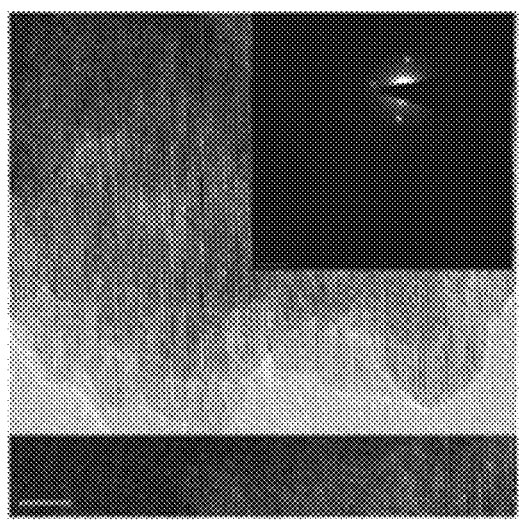
FIGS. 4A and 4B depict HRTEM images of the Meso-ZSM-5 created using the method disclosed.
Figure 4B:
Figure 4C:
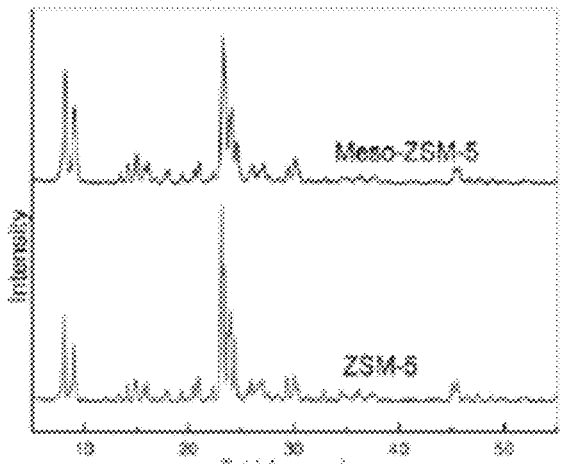
FIGS. 4C to 4F depict, respectively, (4C) XRD patterns for the Meso-ZSM-5, (4D) the amplified XRD patter between $1$-$10°$ of $2\theta$, (4E) $N_2$ sorption isotherms for the Meso-ZSM-5, and (4F) the NLDFT pore size distribution plots of Meso-ZSM-5 and conventional ZSM-5.
Figure 4D:
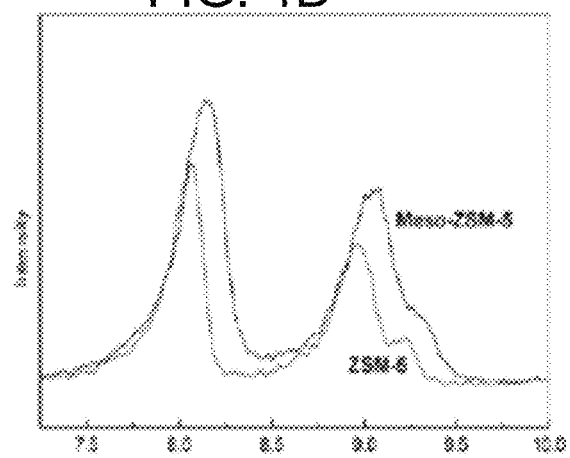

Solid-State Crystallization Evolution and Textural Properties—To reveal the solid-state crystallization evolution, aluminosilicate intermediates at different synthesis moments were examined with SEM, XRD and NMR. The nanogels collected after drying of the nanogels have an average size of ~20-30 nm (FIG. 2a) and are amorphous (FIG. 3). After crystallizing in a solvent-free environment for 3 hours, these nanogels started aggregating in some locations with unclear boundaries (FIG. 2b) while the majority stayed amorphous (FIG. 3). When the crystallization proceeded to 6 hours, weak crystalline peaks appeared (FIG. 3a) with a relative crystallinity of approximately 40% (FIG. 3b). More aluminosilicate ensembles were found with defined boundaries (FIG. 2c). All MFI peaks with strong, clearly defined pattern were first shown after 9-hours of crystallization (FIG. 3) with a relative crystallinity close to approximately 90% (FIG. 3b). At around 9 hours of crystallization, large nanoparticle ensembles with clear boundaries and uniform size were prevalent (FIG. 2d). With a total of 12-hour crystallization, the XRD pattern stayed the same without further increase in the intensity of individual peaks (FIG. 3a). Further extending the crystallization time had no change on the crystallinity degree (FIG. 3b), indicating that fully crystallized zeolites are obtained after the 12-hour, solid-state crystallization. These large zeolites have similar spherical shape, uniform particle size (approximately 400 nm in diameter), and very rough surfaces (FIG. 2e). The high magnification SEM image (FIG. 2f) further reveals that they are highly mesoporous, attributed to the assembly of many nanoparticles of 20-30 nm. High-resolution TEM (HRTEM) images further showed that these are nanosized crystals. Considering their similar size to the original aluminosilicate nanogels, it is hypothesized that each monolithic zeolite nucleates simultaneously from many individual nanogels. The formed small nanocrystals exhibit lattice fringes of the same orientation as the other nanocrystals around them, suggesting that these nanocrystals have been grown and merged into a single, large monolithic crystal rather than randomly packed nanocrystal aggregates. The jointed nanocrystals create many inter-lattice mesopores in zeolite crystalline frameworks. With the XRD pattern of these zeolites matching that from a conventional microporous ZSM-5 sample and in good agreement with the database MFI structure (FIG. 4c), we conclude the successful synthesis of mesoporous ZSM-5 with this new solid-state crystallization approach (denoted as Meso-ZSM-5 in later discussions). Although slightly broader XRD peaks were seen in these Meso-ZSM-5 samples compared to the microporous ZSM-5 samples due to the small individual crystallites (FIG. 4d), their jointed framework as single, monolithic pieces of crystallites of 400 nm largely offsets any pronounced peak broadening effect often seen in physical aggregates of nanosized zeolites. Therefore, identical XRD patterns with similar peak width are found in Meso-ZSM-5 and microporous ZSM-5 of similar crystal sizes (400-500 nm).

Figure 4E:
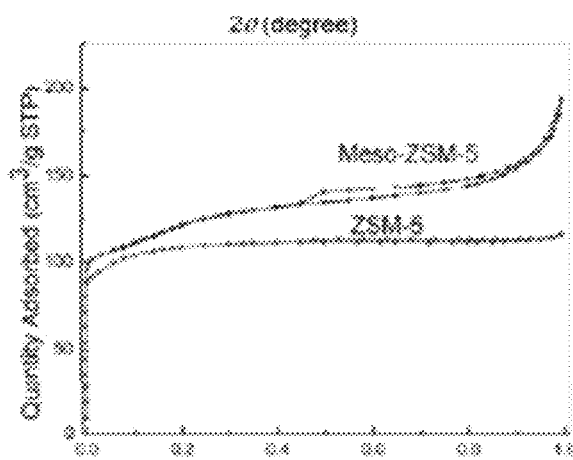
Figure 4F:
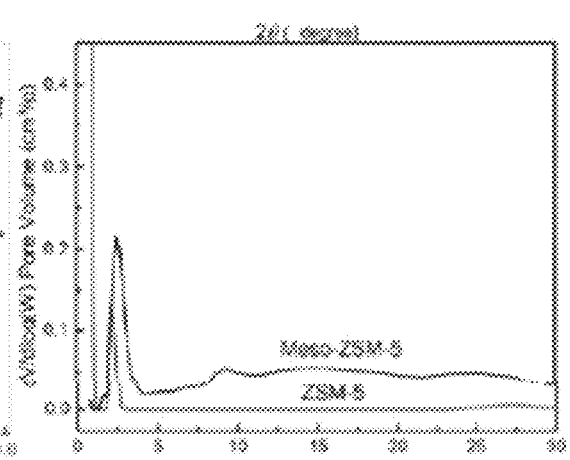

The $N_2$ adsorption-desorption isotherm of the Meso-ZSM-5 zeolite sample was obtained, which exhibits features of both type I and type IV(a) profiles with two steep uptake steps, one at $P/P_0$<0.02 relative pressure and the other at 0.45 relative pressure <$P/P_0$<0.90 relative pressure locations (where $P_0$ is the atmospheric pressure), responding for micropore filling and mesopore capillary condensation, respectively (FIG. 4e). In contrast, the conventional ZSM-5 shows a typical type-I isotherm with only one high uptake at low relative pressures ($P/P_0$<0.02) and a long plateau at high relative pressures (0.4<$P/P_0$<0.9), indicating that the material is a purely microporous phase with negligible mesoporosity. Together with this additional high uptake of the type-IV(a) profile, the appearance of a typical H4 hysteresis loop on the isotherm of typical mesoporous materials at high relative pressure further confirm the existing of both microporosity and mesoporosity in our synthesized Meso-ZSM-5. This H4 loop with more pronounced uptake at low $P/P_0$ than H1 or H2 is consist with the adsorption-desorption isotherms of aggregated nanocrystals of zeolites. In the NLDFT pore size distribution plot, a very sharp peak centered at 3.0 nm, followed by a weak, broad peak centered at 9 nm is found for this Meso-ZSM-5 sample (FIG. 4f). The long tail of the second peak could be the result of mismatching between the actual pore structure and the available model pore shapes. Nonetheless, it endorses the existing of mesopores in Meso-ZSM-5. In contrast, only the first peak centered at 2.0 nm is shown in the NLDFT plot for traditional ZSM-5 sample, consist with its sole microporous structure.

The solid-state $^{29}Si$ and $^{27}Al$ MAS NMR spectra (FIG. 5) were used to investigate the framework formation dynamics of Meso-ZSM-5 through local bonding environment changes. $^{29}Si$ MAS NMR provides information about silicon atoms with different bonding environments in the zeolite framework with silicon atoms connected to silicon, aluminum, or other atoms via oxygen bridges named $Qa_{a+b}$ (bAl) or $Si(OSi)_a(OAl)_b(OH)_{4-(a+b)}$, where a and b are the number of adjacent —OSi and —OAl units attached to Si, respectively. At the beginning of the crystallization, the $^{29}$Si NMR chemical shift spectra show one weak but very broad peak between −80 and −120 ppm due to its amorphous state with silicon atoms connected with multiple hydroxyl group (FIG. 5a). With the crystallization ongoing, this peak becomes narrower and its intensity increases, indicating the formation of Si—O—Si and Si—O—Al bonds. Further extending the crystallization time results in peak split with one peak centered at −113 ppm, identified as Q4(0Al) species, and the other peak at −105 ppm, identified as Q4(1Al) species. $^{27}$Al MAS NMR was also collected to reveal the bonding environment around the aluminum atoms in the framework (FIG. 5b). The spectra feature a chemical shift between 40 and 60 ppm (designated as tetrahedrally coordinated Al) and similar peak evolution (i.e., intensity increases, accompanied with a decrease in the full width at half maximum (FWHM)). A well-defined peak is found at a chemical shift of 54.5 ppm on $^{27}$Al MAS NMR of the fully crystallized sample, confirming the isomorphous substitution of Al in the $SiO_4$ structure. Further comparisons with the $^{29}$Si and $^{27}$Al spectra with microporous ZSM-5 samples show similar chemical shift pattern, except sharper and better resolved Q4(0Al) and Q4(1Al) peaks in $^{29}$Si spectra (FIGS. 5c-5f). This further confirms that the Meso-ZSM-5 formed by the solid-state crystallization process has a similar local bonding environment and framework as traditionally formed ZSM-5.

Discussion on Synthesis Mechanism and Criteria—Although most transformations occur in the solid state crystallization step, the steps prior to that are equally important as they prepare dry, amorphous aluminosilicate nanogels so that precursors can self-assemble into nanoparticle aggregates of appropriate size without initiating crystallization. If the nanogels grow too fast and start crystallizing while the nanogels are drying, they will eventually turn into conventional microporous zeolites in later thermal treatment, just like those obtained in traditional hydrothermal synthesis (FIG. 6a). This occurs if the original mother solution is too basic (i.e., a pH greater than about 14) or the chosen synthesis conditions are very harsh (e.g., high assembly temperature). Besides their amorphous feature, appropriate size is also important for formed nanogels. Nanogels of 100 nm or less (i.e., maintaining a clear solution before drying) are appropriate for solid-state crystallization. Only a structure-directing agent, such as TPAOH, is involved in the solid state crystallization method disclosed herein. Besides its main role as governing crystallization of the MFI framework within the building blocks (i.e., amorphous nanogels), the structure-directing agent (such as TPAOH) also creates and maintains a high pH environment for the dissolution of sodium aluminate. As no substantial liquid water or steam is available for traditional dissolution-addition growth in the solid-state crystallization stage, the dried nanogels obtained using the disclosed method engage in particle-particle interactions, accumulation, and the later solid state crystallization without the requirement of additional controls. The build-up of large ensembles of uniform size from many adjacent nanogels is believed to initiate these transformations. Considering the range of available forces, small nanogels are therefore preferred for particle interactions and attachments. Along with nanogel assembly, the unique supply of needed solvent already present in the nanogels (i.e., water molecules stored in nanogels) also triggers the nucleation and further crystallization in the confined space of each individual nanogel. With the solid crystallization gradually extending to edges of nanocrystals, neighboring nanocrystals orient their lattice pattern to each other and merge into a monolithic crystal. Simultaneously, hierarchical inter-lattice pores are built up between nanocrystals during their periodic piling. Such growth evolution likely follows a new aggregative growth model that is found in silicate-1 growth at ambient conditions (see, T. M. Davis, T. O. Drews, H. Ramanan, C. He, J. Dong, H. Schnablegger, M. A. Katsoulakis, E. Kokkoli, A. V. McCormick, R. L. Penn, M., Tsapatsis, Mechanistic principles of nanoparticle evolution to zeolite crystals. Nat. Mater. 5 (2006) 400-408; S. Kumar, Z. Wang, R. Lee Penn, M. Tsapatsis, A structural resolution cryo-TEM study of the early stages of MFI growth. J. Am. Chem. Soc. 130 (2008) 17284-17286), or more generally, the particle attachment crystallization mechanism seen in natural mineral formation (See, E. Beniash, J. Aizenberg, L. Addadi, S. Weiner, Amorphous calcium carbonate transforms into calcite during sea urchin larval spicule growth. Proc. R. Soc. B-Biol. Sci. 264 (1997) 461-465; Y. U. T. Gong, C. E. Killian, I. C. Olson, N. P. Appathural, A. L. Amasino, M. C. Martin, L. J. Holt, F. H. Wilt, P. U. P. A. Gilbert, Phase transitions in biogenic amorphous calcium carbonate. Proc. Natl. Acad. Sci. U.S.A. 109 (2012) 6088-6093). But unlike these classical assembly and crystallization in geologic or synthetic environments, the present nanoparticle powders, not an aqueous suspension of nanoparticles, are involved in the solid state crystallization approach described herein. In the solid state crystallization, only water stored in the amorphous nanogels participates and mediates the assembly dynamics and crystallization kinetics. In fact, the use of the stored water and its quantity is an important element to create the shown unique hierarchically porous zeolites with jointed crystal framework in this solid-state crystallization process. If substantial free liquid water or steam was introduced in the solid-state crystallization stage, some nanogels would nucleate earlier than others, consume aluminosilicate precursors from surrounding nanogels, and eventually transform into large piece, single crystal zeolites. As a result, a physical mixture of large, microporous zeolites and aluminosilicate nanoparticles would be obtained (FIG. 6b).

Figure 7A:
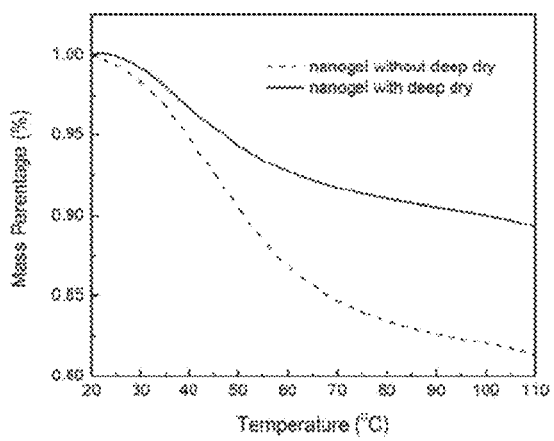
FIGS. 7A and 7B are graphs of (7A) TGA results of nanogels after stage I synthesis with and without further drying and (7B) $NH_3$-TPD results of Meso-ZSM-5 and conventional ZSM-5 zeolites.

Due to the critical role of water pre-stored in nanogels to the success of this solid-state crystallization, TGA was used to quantify the water content in nanogel powders obtained from the method disclosed herein. Water available for later crystallization comes from two different sources: (1) water encapsulated in nanogels by their thick skin after the overnight evaporation process and (2) water adsorbed from the environment as a consequence of significant increase in the total surface area after aluminosilicate gel was ground to powders. To distinguish the amount of water from each source, part of the nanogel sample was kept in an ultra-dry glove box (with water content <0.1 ppm) for a week to eliminate the surface adsorbed water. As shown in FIG. 7a, the total weight loss of nanogel sample without being further dried in glove box is nearly 20% while the one deeply dried shows only ~10% loss of weight. This suggests that in solid-state crystallization, water stored in nanogels occupies approximately 20% of the total gel weight and is sufficient to fully transform aluminosilicates nanogels to zeolite framework. This is significantly less than the steam-assisted crystallization route, in which a water/gel ratio of 10 is commonly used. In addition, as such stored water is fully utilized in nanogel assembly and transformation, no detectable pressure is built up during synthesis, unlike the traditional hydrothermal or steam-assisted crystallization route in which >1.0 MPa steam pressure is generated and high-pressure vessels such as autoclave are required.

Figure 8A:
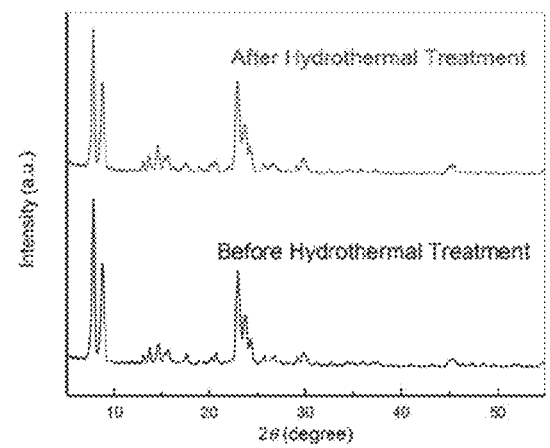
FIGS. 8A to 8D are, respectively, images of the results of hydrothermal stability tests with (8A) showing XRD patterns, (8B) showing SEM image of Meso-ZSM-5 after additional hydrothermal treatment, (8C) showing $^{29}Si$ MAS NMR patterns of Meso-ZSM-5 before and after hydrothermal treatment, and (8D) showing $^{27}Al$ MAS NMR patterns of Meso-ZSM-5 before and after hydrothermal treatment.
Figure 8B:
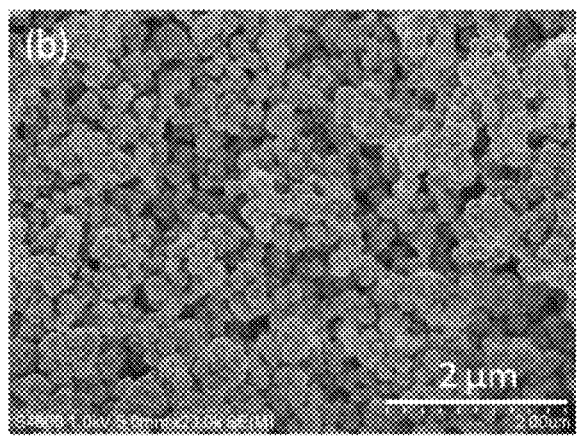

Evaluation of Surface Acidity and Stability—The $NH_3$-TPD analysis was conducted to evaluate the surface acidity of both Meso-ZSM-5 and microporous ZSM-5 samples. As depicted in FIG. 8b, the two profiles are almost identical, with two separated desorption peaks centered at 140° C. and 410° C., which correspond to the weak and strong acid sites of zeolites, respectively. This confirms the similar acidity of Meso-ZSM-5 and microporous ZSM-5, attributed to their similar Si/Al ratios.

Figure 8C:
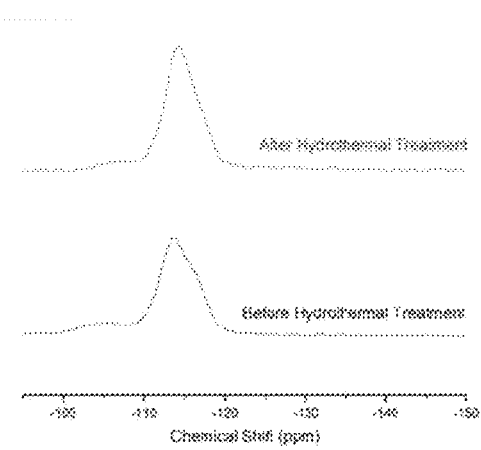
Figure 8D:
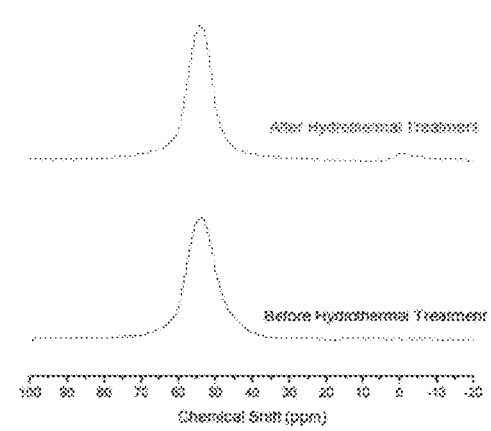
Figure 9A:
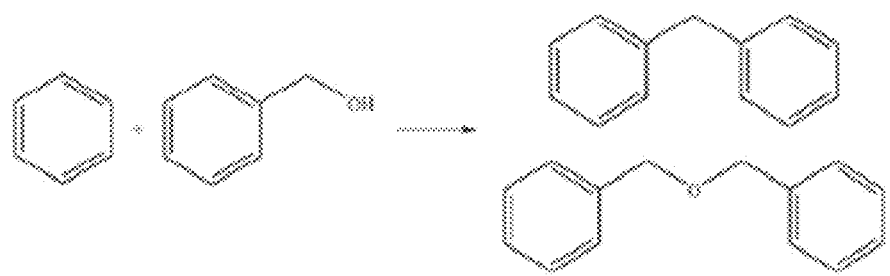
FIG. 9A depicts a diagram of the Friedel-Crafts alkylation of benzene with benzyl alcohol.
Figure 9B:
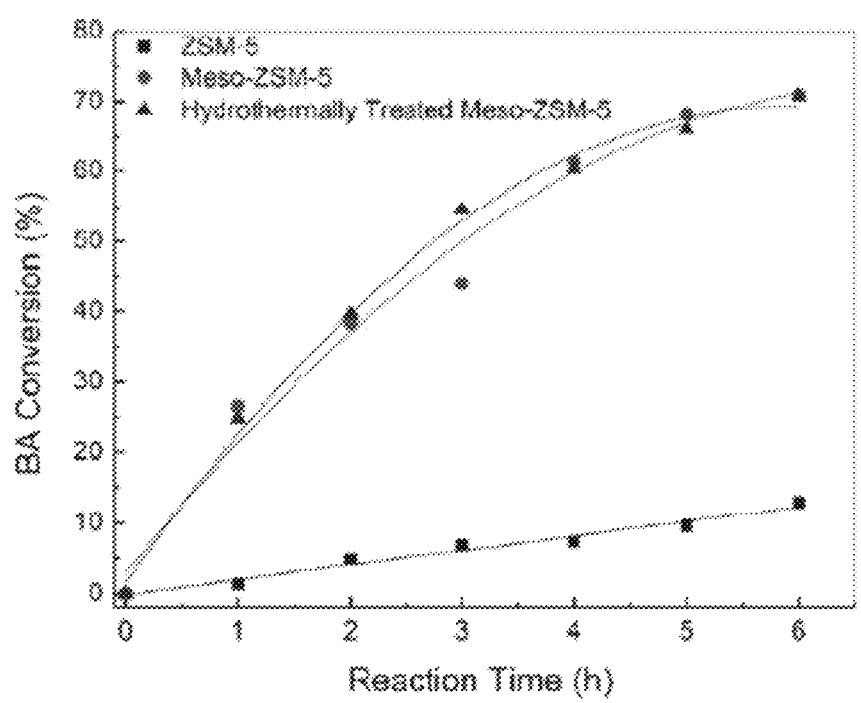
FIG. 9B depicts a graph of the benzyl alcohol conversion of Meso-ZSM-5 compared to conventional ZSM-5.

Unlike mesopores in physically aggregated nanosized crystals, the hierarchical pore structure in Meso-ZSM-5 shows excellent stability after being further hydrothermally treated at 150° C. for 72 hours—the same XRD and NMR patterns and peak intensity are preserved (FIGS. 8a, 8c & 8d), their size and morphology are preserved (FIG. 8b), and the later catalytic activity in the reactions discussed below is also preserved (FIG. 9b). These results indicate that the monolithic Meso-ZSM-5 synthesized by our approach has good hydrothermal stability and retains its catalytic activity even after being hydrothermally treated. It also demonstrates that the solid-state crystallization process is completed after the 12-hour calcination and the produced Meso-ZSM-5 zeolites indeed reach their stable crystalline structure, not just some intermediates collected from the middle of a slow crystallization process.

Evaluation of Catalytic Performance—Although having similar overall acidity, the unique textural features of Meso-ZSM-5 zeolites synthesized by the solid-state crystallization method are expected to promote the utilization of active sites and diffusion of zeolites with bulky reactants and/or products from two different aspects: (i) its nanocrystal building units help expose more accessible active sites of zeolites to bulky molecules and (ii) the connected mesoscale pathways among these jointed nanocrystals reduce the diffusion barriers for these large reactant molecules to reach them and for possible bulky product molecules diffuse out to avoid pore blocking.

Figure 7B:
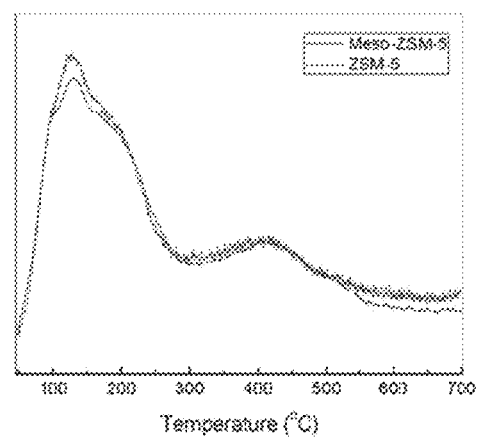

Catalytic Performance in Friedel-Crafts alkylation—The improved catalytic performance of Meso-ZSM-5 was first evaluated with the Friedel-Crafts alkylation of benzene with benzyl alcohol, a typical diffusion-constrained reaction with both bulky reactants and products (FIG. 9a). As shown in FIG. 9b, Meso-ZSM-5 shows a much higher catalytic conversion of benzyl alcohol than the conventional ZSM-5 after a 6-hour reaction at 80° C. (71% for Meso-ZSM-5 versus 11% for ZSM-5). Considering their similar Si/Al ratio (Si/Al=33) and acidity (FIG. 7b), this suggests that the increased catalytic activity of Meso-ZSM-5 is mainly attributed to its mesoporous structure. The connected mesoscale pathways allow bulky reactants (e.g., benzyl alcohol) and products (e.g., diphenylmethane) to transport to the active sites easier. The unique hierarchically porous configuration of Meso-ZSM-5 also provides more accessible active sites on the jointed nanocrystals. Unlike mesopores in physically aggregated nanosized crystals, the hierarchical structure from fused nanocrystals in Meso-ZSM-5 shows excellent stability after being further hydrothermally treated because after being hydrothermally treated it retains the same catalytic activity in the Friedel-Crafts alkylation (FIG. 9b).

Figures 10A, 10B:
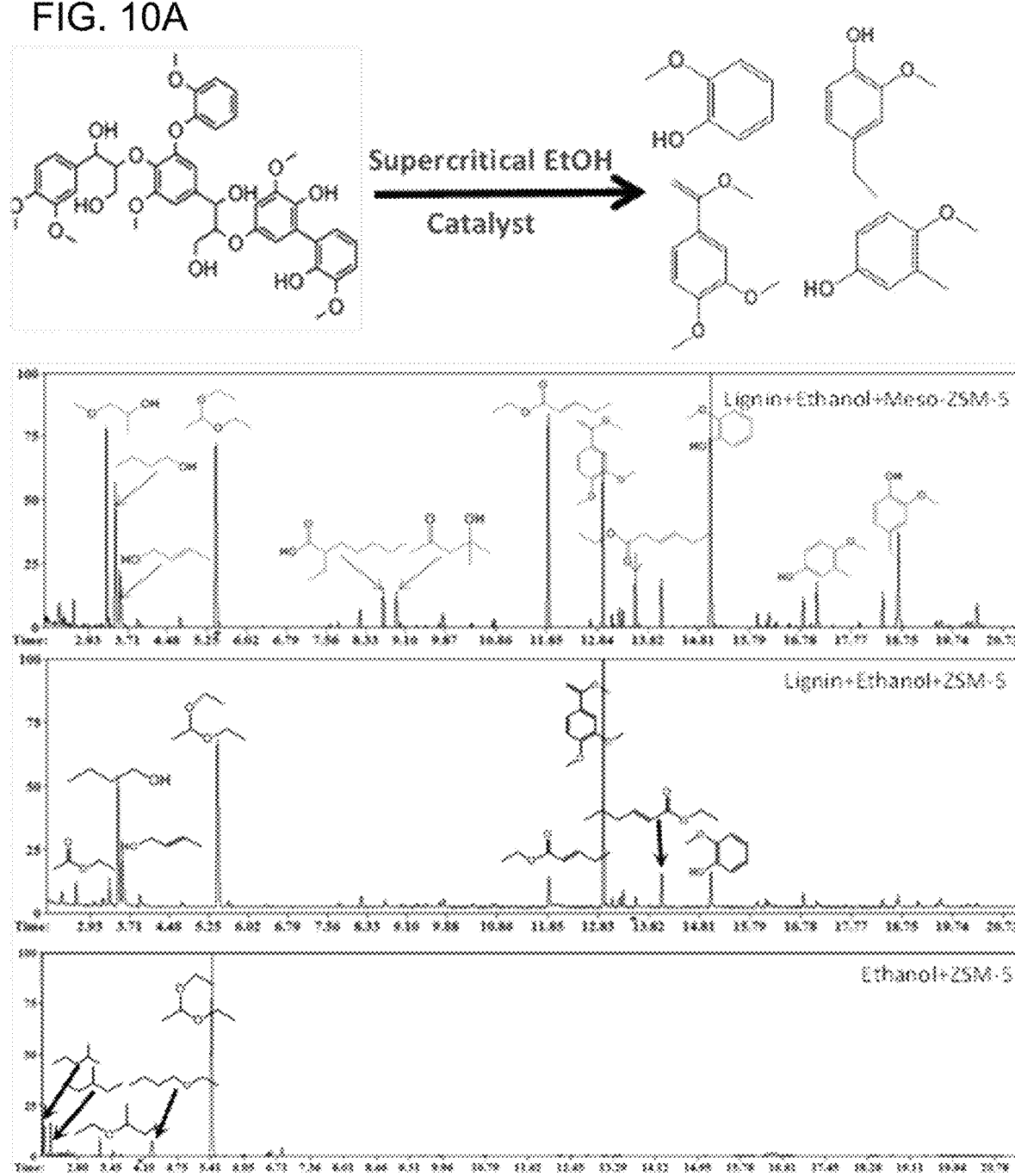
FIG. 10A depicts a schematic of lignin ethanolysis.
FIG. 10B depicts GC-MS spectrums of lignin ethanolysis of Meso-ZSM-5, conventional ZSM-5, and only ethanol and zeolites.
Figure 10C:
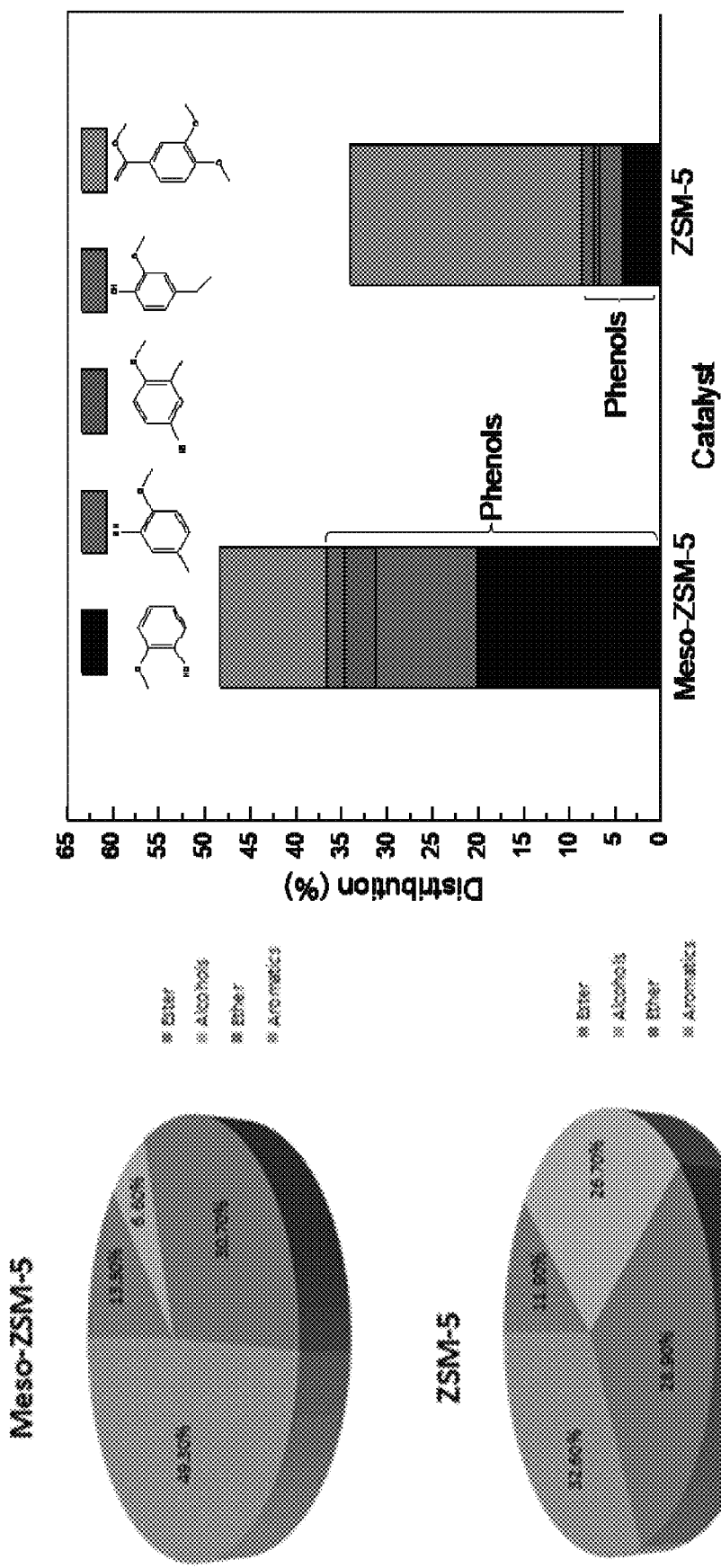

Catalytic Performance in Lignin Depolymerization with Supercritical Ethanol—Considering the large quantity demand of zeolites in biomass conversion processes and the environment-friendly synthesis advantage of our Meso-ZSM-5, the catalytic performance of Meso-ZSM-5 was further evaluated in lignin depolymerization for effective promotions of the transport of giant reactants and/or products. As the second most abundant natural polymer, lignin has long been a high-volume major byproduct and environmental hazard of the paper and pulp industry. Depolymerization of lignin has drawn great attention, not just for its environmental benefits on eliminating such major pollution waste, but also for its promising potentials in producing high-value aromatics as renewable chemicals and fuels. However, cracking lignin fragments to release the rich phenol-type aromatics is not trivial, considering the difficulty on effective cleavage of the many C—O—C and C—C linkages in its molecular structure and diffusion barriers to its truly gigantic fragments. Processes such as hydrolysis, oxidation, and reduction in lignin have been investigated with the help of noble metal and/or hydrotreating catalysts. Among these processes, ethanolysis under supercritical conditions (FIG. 11a) is favorable with its high conversion and no char formation benefits. The ethanolysis of Kraft lignin was carried out in a batch reactor at 280° C. under a pressure of 8 MPa for 6 hours after purging with $N_2$. Similar to benzylation reactions, Meso-ZSM-5 exhibited a higher conversion of lignin (72.5%), when compared to that of ZSM-5 (62.6%) and no tar or char was found. A total of 22 molecules with a mass weight of more than 1.0% of all products were detected by gas chromatography-mass spectrometry (GC-MS), as shown in FIG. 10b. Some products eluted early in the GC-MS spectrum, particularly the three different types of short-chain ether, are mainly derivatives of ethanol reforming reactions in the presence of zeolites. This is verified when comparing the GC-MS spectrum of lignin ethanolysis products with that from reactions involving only ethanol and zeolites at the same conditions (FIG. 10b). Mass spectrum peaks of the other 17 products including different types of alcohol, acetal, and aromatics appeared only when lignin was added. The early eluted compounds in lignin depolymerization samples, with short chains of $C_4$-$C_6$, such as butanol, acetate, and acetal, show similar peak intensity in the GC-MS spectrums for ethanolysis products using Meso-ZSM-5 and microporous ZSM-5. But signals of the later eluted compounds of $C_8$-$C_{11}$, most as aromatics, increase greatly for samples depolymerized by Meso-ZSM-5 than that using microporous ZSM-5 (FIGS. 10b-10d). The high-yield of overall aromatics (49.3% for Meso-ZSM-5 versus 32.6% for ZSM-5) with more diversified individual compounds suggests deeper breakdown of lignin fragments over Meso-ZSM-5 (FIG. 10d). More small, high-valued aromatics, especially desired phenols such as guaiacol (approximately 20%) and alkane substituted guaiacols such as ethylguaiacol and methylguaiacol (approximately 15%), show an increased yield when using the Meso-ZSM-5 catalyst, as shown in FIGS. 10b and 10d. As comparison, the major aromatic product in ethanolysis over traditional microporous ZSM-5 is 1,2-Dimethoxy-4-(1-methoxyethenyl) benzene (approximately 25%), a relatively large intermediate aromatic fragment, together with quite limited phenol-type, small fragments (approximately 6.2%). Similar to what occurs in Friedel-Crafts alkylation, the high phenol selectivity observed in ethanolysis over Meso-ZSM-5 is attributed to their more exposed active sites on their nanosized zeolite building units and the mesoscale connecting channels to them in the monolithic crystal. Large fragments of lignin such as 1,2-Dimethoxy-4-(1-methoxyethenyl)benzene can readily reach the active sites of zeolites for further cracking into smaller fragments (e.g., phenols) before leaving the catalyst surface. Although the reactions occurred in supercritical ethanol, Meso-ZSM-5 zeolites still kept their original size and morphology with no sign of crystal breakage after the 6-hour high-temperature, high pressure reaction (see FIG. 11, which demonstrates the superior stability of Meso-ZSM-5 created using the solid-state crystallization process described herein). It also further supports the conclusion that the edges of nanocrystals in Meso-ZSM-5 are indeed fused together as single monolithic crystals.

Catalytic Performance in Hydrogeneation of Naphthelene—The catalytic performance of Pt/Meso-ZSM-5 catalyst in naphthalene hydrogenation was investigated. The reaction was performed in a batch reactor at 200° C. with a hydrogen pressure of 7.5 MPa. FIG. 12a shows the reaction network of naphthalene hydrogenation, with main compounds as partially hydrogenated tetralin and fully saturated cis- or trans-decalin. As shown in FIG. 12b, the reaction rate of naphthalene is much faster over Pt/Meso-ZSM-5 catalyst than that over Pt/ZSM-5, with the conversion of naphthalene reaching to 100% within 3 hours. In contrast, only approximately 80% of naphthalene is consumed over Pt/ZSM-5 catalyst at the end of a 5-hour reaction time. The hydrogenation of naphthalene to tetralin is much easier than the further hydrogenation of tetralin to decalin, with the reaction rate of the former about 30 times higher than the latter. Hence decalin selectivity is often used as criterion to evaluate the performance of catalyst in naphthalene hydrogenation. From FIG. 12c, no decalin is detected in the hydrogenation product over Pt/ZSM-5. The production of tetralin is also delayed for about an hour when enough naphthalene is converted and then goes up. This confirms the poor deep hydrogenation activity of Pt/ZSM-5 at such low hydrogenation temperature (200° C.). But over Pt/Meso-ZSM-5, there is a quick consumption of naphthalene which results in both tetralin and decalin present in the hydrogenation product even at the early stage. The decalin selectivity continues to increase when more naphthalene is converted and its selectivity exceeds that of tetralin after one hour. Among all decalin products, nearly equal quantity of trans- and cis-decalin presents.

Similar to the other two ZSM-5 catalyzed reactions involved bulky molecules discussed above, the improvement of such naphthalene hydrogenation performance over Pt/Meso-ZSM-5 is attributed to its unique intercrystal pore structure of mesopores and micropores (and macropores resulting from the interconnecting mesopores and micropores) and strong acidity. Compounds involved in naphthalene hydrogenation have molecular sizes between 0.50 and 0.71 nm, which could transport easily in the mesopores of Meso-ZSM-5, while facing significant resistance inside the 10-member ring of traditionally formed ZSM-5 (ZSM-5 having only micropores). On Pt/ZSM-5, poorer hydrogenation capacity is attributed to such diffusion limitation of naphthalene and tetralin in the ZSM-5's micropores. In contrast, the staged hierarchical porosity (i.e., connected macropores, mesopores, and micropores) of Meso-ZSM-5 allows the Pt particles to reach deep to the more exposed surface of zeolites during the wet impregnation. More electron-deficient Pt active centers attributed to effective hydrogenation could also be formed and become accessible in Pt/Meso-ZSM-5 during the partial electron transfer from Pt particles to acidic sites of zeolites, unlike in Pt/ZSM-5 where some Pt active centers and the secondly spillover based hydrogenation pathway cannot be reached. The spillover hydrogen coming from connected micropores in Pt/Meso-ZSM-5 could further promote the hydrogenation of tetralin adsorbed on the acidic sites of zeolites to the saturated decalin before leaving those active sites. This not only proves the excellent deep hydrogenation performance of this new Meso-ZSM-5 catalyst, but the high yield of decalin compounds (the saturated hydrocarbons) may also bring great profit to the oil-refinery and coal liquefaction industries from the perspective of producing high CN fuel such as diesel (CN for naphthalene is 1, tetralin is 10, and decalin is 36) and fuel with superior thermal stability at extreme conditions such as jet fuel.

Zeolite Processing Advantage of this Solid-State Crystallization Process—This solid-state crystallization method described herein provides not only hierarchically porous zeolites with textural features (i.e., such as jointed nanocrystals with inter-crystalline mesovoids) and enhanced catalytic performance in multiple important operations in modern oil-refinery and coal liquefaction industries, but also provides solutions to some severe material, economics, and environmental issues associated with traditional hydrothermal zeolite production routes. Because the solid-state crystallization method involves only solid crystallization and no liquid is loaded and no pressure is built up during crystallization, the crystallization vessel could be fully loaded, which will significantly increase the zeolites yield. Moreover, because the crystallization is carried out at atmospheric pressure, any vessels that are capable of tight seal at elevated temperature and resistant to basic liquid can be used, unlike traditional hydrothermal or steam-assisted crystallization, in which high-pressure vessels such as autoclave is mandatory. This will significantly save cost on the synthesis equipment as well as its operation. In addition, this largely reduces the liquid pollution generated in traditional hydrothermal zeolite synthesis, in which a large percentage of alkali, silicates, and aluminates are left in the post-synthesis solution. These unused chemicals not only lower the overall zeolite yield, but also generate a large amount of waste liquid. The recovery of these unused chemicals is difficult and costly and the chemicals can cause severe environmental pollution. In contrast, the method described herein integrates all silicates and aluminates into the nanogels and carries out crystallization only using the dried nanogels. This eliminates the requirement for even a small amount of water. The fact that all silicates and aluminums are integrated into nanogels which are then dried (and optionally ground into powders) helps increase zeolite yield, and more importantly, produces almost no liquid waste to the environment. Also, neither hard meso-template nor special soft meso-template materials are involved in our approach. The solid-state crystallization method described herein not only significantly lowers the production cost, but also simplifies the synthesis procedures. Although a structure directing agent such as TPAOH, is used, they are encapsulated in nanogels and later produced zeolites during synthesis and are removed during zeolite calcination.

In summary, the method disclosed herein produces a hierarchically porous Meso-ZSM-5 zeolite using a two-stage synthesis process with solid-state crystallization without the use of a meso-template. The resulting zeolites have excellent hydrothermal stability and superior catalytic performance in reactions such as Friedel-Crafts alkylations, lignin depolymerization in supercritical ethanol, and deep hydrogenation of naphthalene, all involving bulky aromatic molecules, compared with conventionally prepared microporous ZSM-5. Meso-ZSM-5's unique solid crystallization conditions simplify the synthesis of zeolites, reduce the production cost, and avoid common liquid pollution issues in the zeolite industry.

What is claimed is:
1. A method of making zeolites comprising the steps of:
 a) providing an aluminosilicate nanogel in a solvent, wherein the aluminosilicate nanogel comprises a structure directing agent;

b) evaporating the solvent to form a plurality of dried nanogels comprising less than or equal to about 30% solvent by weight; and c) heating the dried nanogels until a plurality of crystallized zeolites, having an average diameter of less than or equal to about 15 μm, are formed.

2. The method of claim 1, wherein step a) further comprises preparing an aluminosilicate nanogel by mixing an aluminum containing precursor, a silicon containing precursor, a structure directing agent, and at least one solvent to create a solution and heating the solution between about 70° and 90° C. for at least about 12 hours.

3. The method of claim 2, wherein the aluminum containing precursor comprises $NaAlO_2$, the silicon containing precursor comprises tetraethylorthosilicate, the structure-directing agent comprises tetrapropyl ammonium hydroxide, and the solvent comprises water.

4. The method of claim 3, wherein the aluminum containing precursor consists essentially of $NaAlO_2$, the silicon containing precursor consists essentially of tetraethylorthosilicate, the structure-directing agent consists essentially of tetrapropyl ammonium hydroxide, and the solvent consists essentially of water.

5. The method of claim 2, wherein step a) further comprises preparing an aluminosilicate nanogel by mixing an aluminum containing precursor, a silicon containing precursor, a structure directing agent, and at least one solvent to create a solution and heating the solution at a temperature between about 70-90° C. for no more than about 36 hours.

6. The method of claim 5, wherein step b) further comprises drying the aluminosilicate nanogel between about 20 to 25° C. for at least 12 hours.

7. The method of claim 1, wherein step a) further comprises preparing an aluminosilicate nanogel by mixing an aluminum containing precursor, a silicon containing precursor, a structure directing agent, and a solvent to create a solution and heating the solution between about 70° and 90° C. until the nanogels are approximately 100 nm or less.

8. The method of claim 1, wherein step b) further comprises drying the aluminosilicate nanogels at less than or equal to about 100° C.

9. The method of claim 8, wherein the crystallized zeolites have an average particle diameter between about 200 nm and 15 μm.

10. The method of claim 8, wherein the dried nanogels are heated until at least 60 percent of the dried nanogels have undergone crystallization.

11. The method of claim 1, wherein in step b) further comprises drying the aluminosilicate nanogels until at least 90 percent of the dried nanogels are under about 100 nm in diameter.

12. The method of claim 1, step c) further comprises heating the dried nanogels between about 90-180° C. for at least about 6 hours.

13. The method of claim 12, further comprising step:

d) drying the crystallized zeolites between about 90-120° C. for at least about 2 hours.

14. The method of claim 1, wherein step b) further comprises grinding the dried nangels into a powder and step c) further comprises heating the powder until a plurality of crystallized zeolites, having an average diameter of between about 200 nm and 15 μm, are formed.

15. The method of claim 1, wherein the crystallized zeolite comprises a MFI structure.

16. The method of claim 15, wherein the crystallized zeolite comprises ZSM-5.

17. A method of making ZSM-5 zeolites comprising the steps of:

a) mixing a structure directing agent, $NaAlO_2$, tetraethylorthosilicate, and a solvent to create a solution;

b) heating the solution at less than or equal to about 100° C. and about atmospheric pressure to form a plurality of aluminosilicate nanogels of 100 nm or less;

c) evaporating the solvent from the aluminosilicate nanogels to form a plurality of dried nanogels comprising about 30% or less solvent by weight;

d) grinding the dried nanogels into a powder;

e) heating the powder between about 90° C. and about 180° C. for at least about 6 hours to form a plurality of crystallized zeolites;

f) drying the crystallized zeolites at about 150° C. or less for at least about 3 hours; and g) heating the crystallized zeolites between about 480° C. and 620° C. for at least 5 hours.

18. The method of claim 17, wherein the structure directing agent comprises tetrapropyl ammonium hydroxide and the solvent comprises water.

19. The method of claim 18, wherein step a) further comprises dissolving the tetrapropyl ammonium hydroxide and $NaAlO_2$ in water to create a solution and then adding tetraethylorthosilicate to the solution while agitating the solution at about 400 to 600 rpm.

20. The method of claim 17, wherein step g) further comprises heating the crystallized zeolites at a rate of about 1-10° C. per minute until a temperature of about 500° is reached and maintaining the crystallized zeolites at about 500° C. for at least about 6 hours.

* * * * *